US008683944B2

(12) United States Patent
Jo et al.

(10) Patent No.: US 8,683,944 B2
(45) Date of Patent: Apr. 1, 2014

(54) INDOOR ARTIFICIAL BREEDING METHOD OF TERMITE

(75) Inventors: Chang Wook Jo, Daejeon (KR); Young-Hee Kim, Daejeon (KR); Jin Young Hong, Daejeon (KR); Mi Hwa Jung, Daejeon (KR); Jung Eun Choi, Daejeon (KR); So Young Jeong, Daejeon (KR)

(73) Assignee: Republic of Korea (National Research Institute of Cultural Heritage), Daejeon (KR)

( * ) Notice: Subject to any disclaimer, the term of this patent is extended or adjusted under 35 U.S.C. 154(b) by 0 days.

(21) Appl. No.: 13/819,435

(22) PCT Filed: Aug. 4, 2011

(86) PCT No.: PCT/KR2011/005726
§ 371 (c)(1),
(2), (4) Date: Feb. 27, 2013

(87) PCT Pub. No.: WO2013/005882
PCT Pub. Date: Jan. 10, 2013

(65) Prior Publication Data
US 2013/0152860 A1   Jun. 20, 2013

(30) Foreign Application Priority Data
Jul. 7, 2011   (KR) .................. 10-2011-0067382

(51) Int. Cl.
*A01K 67/00*   (2006.01)
(52) U.S. Cl.
USPC ........................................... 119/6.5

(58) Field of Classification Search
USPC ............................................ 119/6.5, 6.6, 6.7
See application file for complete search history.

(56) References Cited

U.S. PATENT DOCUMENTS

| | | | | |
|---|---|---|---|---|
| 2,151,589 | A | * | 3/1939 | Falls .............................. 119/6.5 |
| 3,687,110 | A | * | 8/1972 | Braunhut ....................... 119/6.5 |
| 4,212,267 | A | * | 7/1980 | Patterson ....................... 119/6.5 |
| 4,363,798 | A | * | 12/1982 | D'Orazio ........................ 424/84 |
| 4,790,260 | A | * | 12/1988 | Jones ............................. 119/6.5 |
| 5,178,094 | A | * | 1/1993 | Carr et al. ....................... 119/6.5 |
| 5,784,991 | A | * | 7/1998 | Ukishiro et al. ............... 119/6.5 |
| 5,927,230 | A | * | 7/1999 | Frank et al. .................... 119/6.5 |
| 6,203,811 | B1 | * | 3/2001 | McPherson et al. .......... 424/405 |
| 7,122,176 | B2 | * | 10/2006 | Stamets .......................... 424/84 |

(Continued)

FOREIGN PATENT DOCUMENTS

| | | |
|---|---|---|
| JP | 07-255324 | 10/1995 |
| JP | 2001-112374 | 4/2001 |
| KR | 10-2002-0029031 | 4/2002 |

OTHER PUBLICATIONS

Connétable et al., "Dispersal Flight and Colony Development in the Fungus-Growing Termites *Pseudacanthotermes spiniger* and *P. militaris*," *Insect. Soc.*, vol. 59:269-277, 2012.

(Continued)

*Primary Examiner* — Yvonne Abbott
(74) *Attorney, Agent, or Firm* — Klarquist Sparkman, LLP

(57) ABSTRACT

Provided is a method of collecting wild termites and rearing the termites indoors. The method can be used to observe physiological and ecological characteristics of termites that give serious damage to wooden cultural assets and buildings, and thus basic information can be obtained for controlling termites.

10 Claims, 5 Drawing Sheets

(56) References Cited

U.S. PATENT DOCUMENTS

| | | | |
|---|---|---|---|
| 7,878,146 B2* | 2/2011 | Vadis | 119/6.5 |
| 7,951,389 B2* | 5/2011 | Stamets | 424/406 |
| 8,097,248 B2* | 1/2012 | Bolckmans et al. | 424/93.7 |

OTHER PUBLICATIONS

Lee, Ecological Characteristics of Termite (*Reticulitermes speratus kyushuensis*) and its Control for Preservation of Wooden Cultural Properties, Chang-Ang University, Jun. 2004.

* cited by examiner

INDOOR ARTIFICIAL BREEDING METHOD OF TERMITE

CROSS REFERENCE TO RELATED APPLICATIONS

This is the U.S. National Stage of International Application No. PCT/KR2011/005726, filed Aug. 4, 2011, published in English under PCT Article 21(2), which claims the benefit of Korea Patent Application No. 10-2011-0067382, filed Jul. 7, 2011, which is herein incorporated by reference in its entirety.

TECHNICAL FIELD

The present invention relates to a method of rearing termites indoors, and more particularly, to a method of efficiently rearing termites indoors by using a culturing container under predetermined conditions.

BACKGROUND ART

Cultural assets around us may be classified according to materials into metallic, stone, wood, paper, fiber cultural assets, etc. Such cultural assets may be variously damaged with time according to the material properties and preservation conditions of the cultural assets. Most of cultural assets having their original forms are also being weathered by rain, wind, sunlight, etc, and damaged by careless managers and visitors. Particularly, cultural assets made of organic materials such as papers, fibers, and woods are further damaged by biological attacks of insects and microorganisms. Therefore, such organic cultural assets should be preserved more carefully as compared with inorganic cultural assets.

In the case where cultural assets are damaged by biological attacks, particularly, insects, materials of the cultural assets are eaten. Since such damage is significant although it may occur sporadically, insect control is a common and important method of preserving indoor and outdoor cultural assets.

Insects harmful to wood, paper, and fiber cultural assets include: isoptera, coleoptera, thysanura, blattaria, hymenoptera, and psocoptera. Particularly, isoptera and coleoptera are more harmful.

Termites (e.g., *Reticulitermes speratus*) are social insects living in colonies and having social classes starting from queen. Termites settle in one place for thirty years or more and do harm to human. According to worldwide reports, termites do harm to timber, wooden houses, wooden telephone poles, wooden bridges, railroad ties, and even crops. In Korea, national treasures such as a national treasure of Haein Temple in Kyeongsangnam-do have been damaged by termites.

In addition to damage by termites, wooden cultural assets are damaged by wood-rot fungi. This causes structural and authentic problems (Kyuhyuk Kim et al. 1999). Wood-rot fungi include white-rot fungi, brown-rot fungi, and mold fungi, which cause tissues of wood to dry, rot, crack, degenerate into sponge, downy hair, or powder, and discolor (Savluchinske-Feio et al. 2007).

In general, cultural assets can be protected from insects as follows. First, cultural assets should be periodically maintained. Secondly, if it is considered that a cultural asset is damaged by insects, the physiological and ecological characteristics and nature of the insects should be investigated to identity the insects. Thirdly, the insects should be controlled by selecting and applying a proper method that does not harm to the quality of the cultural asset according to the kind of the insects.

Therefore, it is necessary to establish a rearing method for termites which have not been artificially reared, so as to effectively investigate the physiological and ecological characteristics and natures of harm insects.

Thus, the inventors have been tried to find a method of rearing wild termites indoor for observing the physiological and ecological characteristics and nature of the termites. As a result, the inventors have invented an efficient method of rearing termites. The method includes the steps of: placing an old tree in which termites live into a rearing box; and keeping the rearing box dark at a temperature of 20° C. to 25° C. and a humidity of 70% to 90%.

DISCLOSURE

Technical Problem

One object of the present invention is to provide a method of rearing termites.

Technical Solution

In order to achieve the object, the present invention provides a method of rearing termites, the method including the steps of:

1) placing termites and an old tree in a rearing box; and
2) keeping the rearing box dark at a temperature of 20° C. to 25° C. and a humidity of 70% to 90%.

The present invention also provides a method of rearing termites, the method including:

1) placing termites, a wood-rot fungus, and an old tree in a rearing box; and
2) keeping the rearing box dark at a temperature of 20° C. to 25° C. and a humidity of 70% to 90%.

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, specific embodiments of the present invention will be described in detail with reference to the accompanying drawings.

There is provided a method of rearing termites. The method includes the steps of:

1) placing termites and an old tree in a rearing box; and
2) keeping the rearing box dark at a temperature of 20° C. to 25° C. and a humidity of 70% to 90%.

In the step 1), it is preferably that the bottom of the rearing box is covered with soil to a thickness of 3 cm to 8 cm so as to suppress evaporation of moisture from the old tree. More preferably, the bottom of the rearing box is covered with soil to a thickness of 4 cm to 7 cm. Even more preferably, the bottom of the rearing box is covered with soil to a thickness of 5 cm. However, the present invention is not limited thereto.

It is preferable that soil is one selected from the group consisting of clay soil, sand soil, sand clay, Hyuga soil, Aakadama soil, Kiryu sand, humus, and Kanuma soil. More preferably, the soil is humus. However, the present invention is not limited thereto.

In the step 1), it is preferable that the old tree is prepared by sterilizing and drying an old tree and impregnating the old tree with distilled water in a vacuum. However, the present invention is not limited thereto.

In the step 2), it is preferable that the rearing box is kept in the temperature range of 21° C. to 24° C., more preferably, at 22° C. However, the present invention is not limited thereto.

In the step 2), it is preferable that the rearing box is kept in the humidity range of 75% to 85%, more preferably, at a humidity of 80%. However, the present invention is not limited thereto.

It is preferably that the termites are in the family mastotermitidae, termopsidae, kalotermitidae, hodetermitidae, rhinotermitidae, or termitidae. More preferably, the termites are in *Reticulitermes speratus* or *Reticulitermes speratus* kyushuensis Morimoto. Even more preferably, the termites are in *Reticulitermes speratus*. However, the present invention is not limited thereto.

It is preferable that the rearing box is 20 cm to 40 cm in length, 20 cm to 40 cm in width, and 30 cm to 50 cm in height. More preferably, the rearing box is 25 cm to 35 cm in length, 25 cm to 35 cm in width, and 35 cm to 45 cm in height. Even more preferably, the rearing box is 30 cm×30 cm×40 cm in length, width, and height. However, the present invention is not limited thereto.

It is preferable that the may be rearing box is formed of medium density fiberboard (MDF), plywood, iron plate, acryl, Foamex, glass, Lexan, or polyvinyl chloride (PVC). More preferably, the may be disposed on is formed of a transparent acryl plate. However, the present invention is not limited thereto.

It is preferable that the rearing box has a rectangular parallelepiped, cube, or cylindrical shape. More preferably, the rearing box has a rectangular parallelepiped shape. However, the present invention is not limited thereto.

It is preferable that the rearing box includes a mesh cover for ventilation. More preferably, the mesh cover is a 13.5 cm×13.5 cm steel mesh cover. However, the present invention is not limited thereto.

A material such as a live plant such as a live tree, a dead plant such as a dead tree, rotting and decomposing humus soil, other termites of a colony, algae, and lichen may be additionally placed in the rearing box as a food for the termites. However, the present invention is not limited thereto.

It is preferable that the mesh cover has a rectangular, square, or circular shape. More preferably, the mesh cover has a square shape. However, the present invention is not limited thereto.

It is preferable that holes of the mesh cover are 0.1 cm to 1 cm in length, and 0.1 cm to 1 cm in width. More preferably, the holes of the mesh cover are in 0.1 cm to 0.4 cm in length, and 0.1 cm to 0.4 cm in width. Even more preferably, the holes of the mesh cover are 0.2 cm in length and 0.2 cm in width. However, the present invention is not limited thereto.

The present invention also provides a method of rearing termites, the method including:

1) placing termites, a wood-rot fungus, and an old tree in a rearing box; and 2) keeping the rearing box dark at a temperature of 20° C. to 25° C. and a humidity of 70% to 90%.

In the step 1), it is preferably that the bottom of the rearing box is covered with soil to a thickness of 3 cm to 8 cm so as to suppress evaporation of moisture from the old tree. More preferably, the bottom of the rearing box is covered with soil to a thickness of 4 cm to 7 cm. Even more preferably, the bottom of the rearing box is covered with soil to a thickness of 5 cm. However, the present invention is not limited thereto.

The soil may be one selected from the group consisting of clay soil, sand soil, sand clay, Hyuga soil, Aakadama soil, Kiryu sand, humus, and Kanuma soil. For example, the soil may be humus. However, the present invention is not limited thereto.

In the step 1), it is preferable that the old tree is prepared by sterilizing and drying an old tree and impregnating the old tree with distilled water in a vacuum. However, the present invention is not limited thereto.

In the step 2), it is preferable that the rearing box is kept in the temperature range of 21° C. to 24° C., more preferably, at 22° C. However, the present invention is not limited thereto.

In the step 2), it is preferable that the rearing box is kept in the humidity range of 75% to 85%, more preferably, at a humidity of 80%. However, the present invention is not limited thereto.

It is preferably that the termites are in the family mastotermitidae, termopsidae, kalotermitidae, hodetermitidae, rhinotermitidae, or termitidae. More preferably, the termites are in *Reticulitermes speratus* or *Reticulitermes speratus* kyushuensis Morimoto. Even more preferably, the termites are in *Reticulitermes speratus*. However, the present invention is not limited thereto.

It is preferable that the rearing box is 20 cm to 40 cm in length, 20 cm to 40 cm in width, and 30 cm to 50 cm in height. More preferably, the rearing box is 25 cm to 35 cm in length, 25 cm to 35 cm in width, and 35 cm to 45 cm in height. Even more preferably, the rearing box is 30 cm×30 cm×40 cm in length, width, and height. However, the present invention is not limited thereto.

It is preferable that the may be rearing box is formed of medium density fiberboard (MDF), plywood, iron plate, acryl, Foamex, glass, Lexan, or polyvinyl chloride (PVC). More preferably, the may be disposed on is formed of a transparent acryl plate. However, the present invention is not limited thereto.

It is preferable that the rearing box has a rectangular parallelepiped, cube, or cylindrical shape. More preferably, the rearing box has a rectangular parallelepiped shape. However, the present invention is not limited thereto.

It is preferable that the rearing box includes a mesh cover for ventilation. More preferably, the mesh cover is a 13.5 cm×13.5 cm steel mesh cover. However, the present invention is not limited thereto.

A material such as a live plant such as a live tree, a dead plant such as a dead tree, rotting and decomposing humus soil, other termites of a colony, algae, and lichen may be additionally placed in the rearing box as a food for the termites. However, the present invention is not limited thereto.

It is preferable that the mesh cover has a rectangular, square, or circular shape. More preferably, the mesh cover has a square shape. However, the present invention is not limited thereto.

It is preferable that holes of the mesh cover are 0.1 cm to 1 cm in length, and 0.1 cm to 1 cm in width. More preferably, the holes of the mesh cover are in 0.1 cm to 0.4 cm in length, and 0.1 cm to 0.4 cm in width. Even more preferably, the holes of the mesh cover are 0.2 cm in length and 0.2 cm in width. However, the present invention is not limited thereto.

It is preferable that the wood-rot fungus is *Trametes versicolor* or *Tyromyces palustris*. However, the present invention is not limited thereto.

In an example according to the present invention, wild termites were collected and placed in a rearing box, and the rearing box was kept dark at a temperature of 22° C. and humidity of 80% (refer to FIGS. 1 and 2), so as to observe physiological ecological characteristics of a colony of wild termites.

In another example according to the present invention, effects of two kinds of wood-rot fungi on termites were observed. First, two kind of wood-rot fungi (*Trametes versicolor* and *Tyromyces palustris*) were incubated. Then, termites and a wood sample (food of termite) were placed together with the *Trametes versicolor*, and termites and a wood sample were placed together with the *Tyromyces palustris*. Thereafter, changes of the total weights and change of the weights of the wood samples were measured. The total weights were reduced in both cases of the *Trametes versicolor* and the *Tyromyces palustris*. However, the weight of the wood sample was increased in the case of the *Tyromyces palustris* although the weight of the wood sample was decreased in the case of the *Trametes versicolor*. In addition, so as to measure how much the wood samples are eaten by the termites, the weight of the wood samples were measured after drying the wood samples. In this case, the weight of the wood sample placed together with the *Tyromyces palustris* was reduced more than the weight of the wood sample placed in the *Trametes versicolor*. Thus, it could be understood that the *Tyromyces palustris* rotted and dampened the wood sample more than the *Trametes versicolor* (refer to FIGS. 3 through 6). That is, wooden buildings may be damaged much more by the combination of termites and *Tyromyces palustris*.

Therefore, the method of rearing termites indoors of the present invention may be usefully used to collect basic data necessary for controlling termites by observing physiological and ecological characteristics of termites reared by the method.

Advantageous Effects

According to the present invention, termites can be reared indoors to observe physiological and ecological characteristics of the termites so as to use the observed data as reference material for controlling termites.

DESCRIPTION OF DRAWINGS

The above and other objects, features and other advantages of the present invention will be more clearly understood from the following detailed description taken in conjunction with the accompanying drawings, in which.

BEST MODE

Hereinafter, examples of the present invention will be illustratively explained.

However, the present invention is not limited to the following examples.

Example 1

Rearing of *Reticulitermes Speratus*

<1-1> Collection of *Reticulitermes Speratus*

Termites (*Reticulitermes speratus*) were collected at Mt. Hwabong, Doryong-dong, Yuseong-gu, Daejeon, Korea, together with surrounding soil and an old tree (old needle tree), so as to observe physiological and ecological characteristics of the termites while rearing the termites indoors.

<1-2> Artificial Rearing of *Reticulitermes Speratus*

Figure 1:
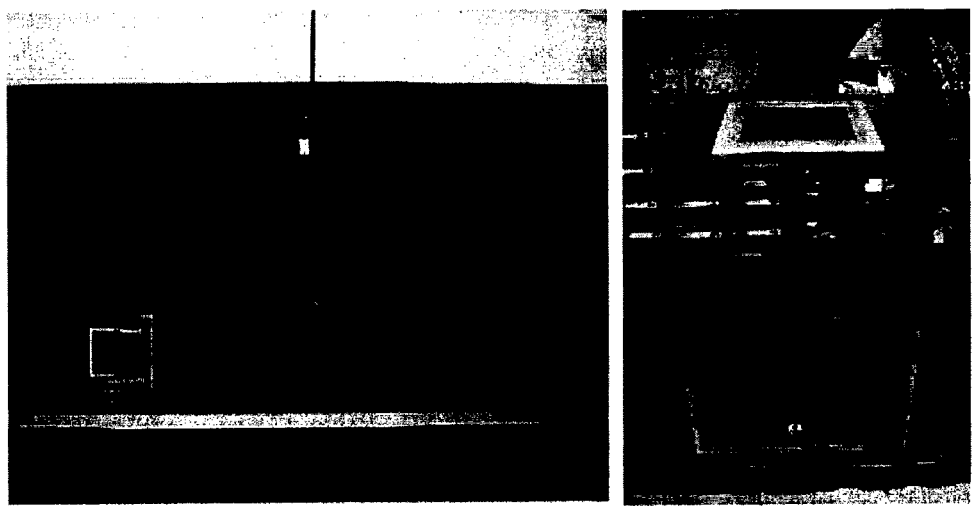
FIG. 1 shows an image (right) of an acryl rearing box (30×30×40 cm in length, width, and height) for rearing termites and an image (left) of a dark chamber in which termites are actually reared.

Artificial rear environments were prepared by making an acryl rearing box (refer to FIG. 1) of 30 cm×30 cm×40 cm (length×width×height), and installing a steel mesh of 13.5 cm×13.5 cm (length×width) on a lid of the rearing box for ventilation. Then, the bottom of the rearing box was covered with the soil collected above <1-1> to a thickness of 5 cm for the purposes of suppressing evaporation of moisture from the old tree, supplying moisture to the old tree, and providing shelter to the termites, and the old tree was placed in the rearing box together with an old tree in which the termites live. Food for the termites was prepared as follows. The old tree collected in <1-1> was sterilized by placing the old tree in a high-pressure sterilizer at 120° C. for 30 minutes, and then was dried in a drier at 120° C. for two days. Thereafter, the old tree was placed in a desiccator together with distilled water and was impregnated with the distilled water by apply a vacuum to the desiccator using Rocker 300 (Gaeseong Scientific Co.) so that the termites fond of wet wood could easily take moisture and nutrition. Since termites live in very dump and rotten old trees, it is important to keep the humidity in a proper range when rearing termites. In addition, if the humidity is too high, fungi may appear. Thus, the rearing box was kept dark at 22° C. and a humidity of 80% (refer to FIG. 1).

Example 2

Effects of Wood-Rot Fungi on Inhabitation of Termites

Figure 2:
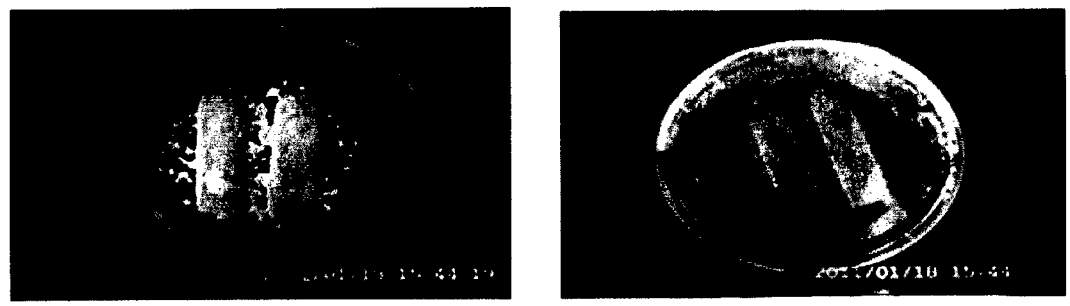
FIG. 2 shows an image (left) taken from *Trametes versicolor* incubated for a month and an image (right) of *Tyromyces palustirs* incubated for a month.

Effects of two kinds of wood-rot fungi (*Trametes versicolor* and *Tyromyces palustris*) on termites were observed as follows. The two kinds of wood-rot fungi were incubated in Petri dishes for one month (refer to FIG. 2). Then, five soldier termites, forty five worker termites, and wood samples were placed in each of the Petri dishes. The Petri dishes were weekly observed for twelve weeks while measuring the weights of the wood-rotting fungi. In addition, the weights of the wood samples were measured after and before the experiment.

Figure 5:
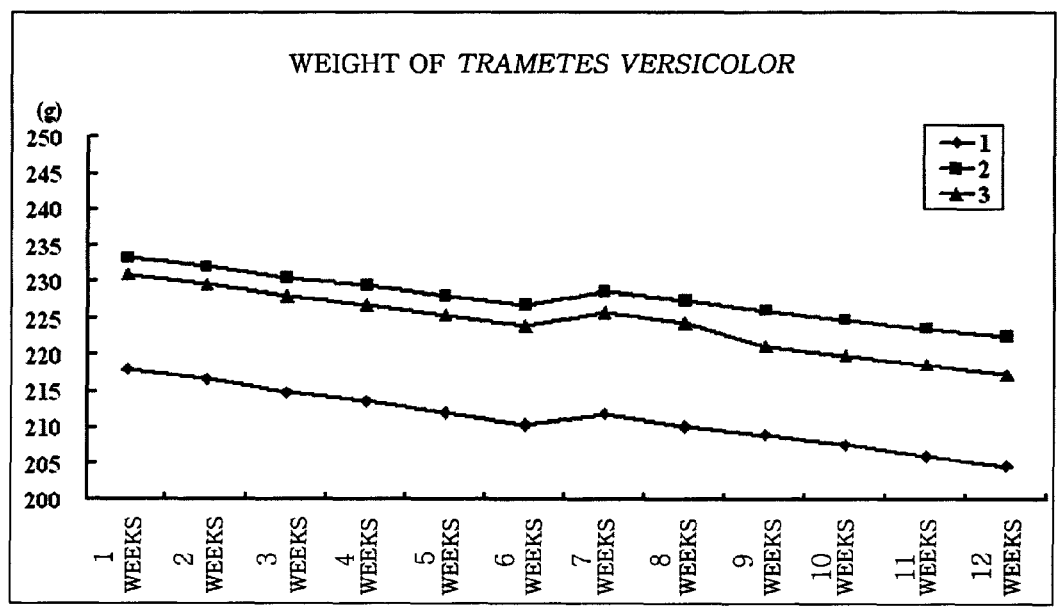
FIG. 5 is a graph showing the weight of *Trametes versicolor* that decreases after the *Trametes versicolor* is incubated together with termites.
Figure 6:
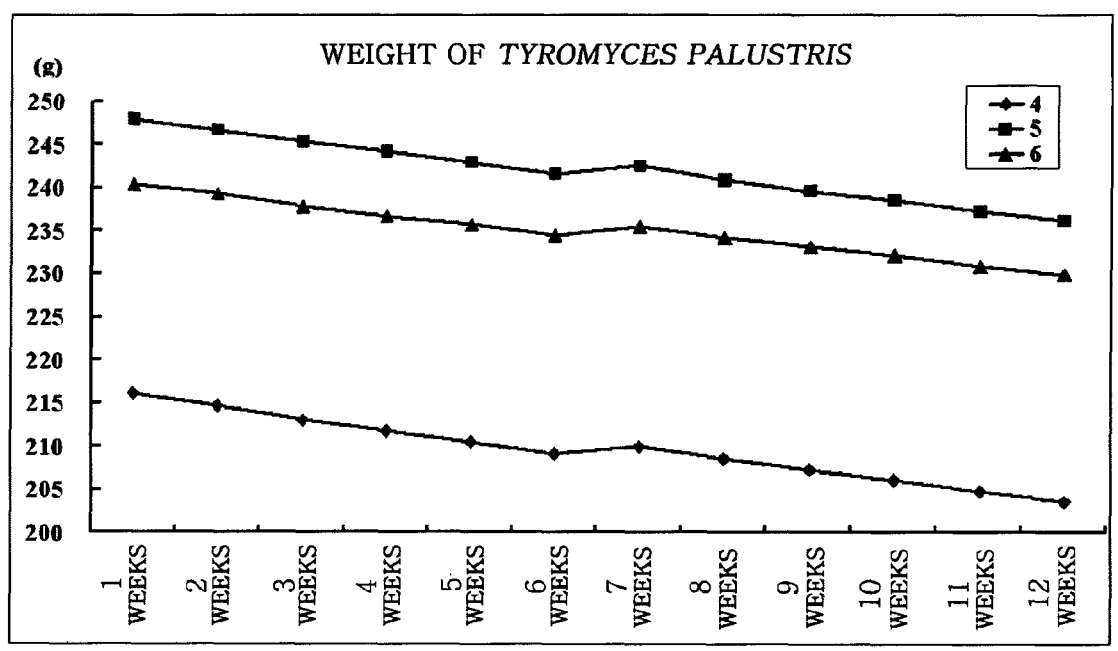
FIG. 6 is a graph showing the weight of *Tyromyces palustirs* that decreases after the *Trametes versicolor* is incubated together with termites.

As shown in FIGS. 5 and 6, the weights of the wood-rot fungi were decreased with time. The weights of the wood samples were decreased in the Petri dishes in which the *Trametes versicolor* was incubated. However, the weights of the wood samples were increased in two Perish dishes in which the *Tyromyces palustris* was incubated (refer to Table 1). The weights of the wood samples might be increased because the wood samples contained much moisture due to the *Tyromyces palustris*.

TABLE 1

| Weight of Impregnated Wood [g] | Before Exp. [g] | After Exp. [g] | Decrease Rate [%] |
| --- | --- | --- | --- |
| *Trametes* | 42.74 | 40.09 | 6.20 |
| *versicolor* | 56.08 | 55.41 | 1.20 |
|  | 53.69 | 51.42 | 4.49 |
| *Tyromyces* | 43.12 | 41.15 | 4.57 |

TABLE 1-continued

| Weight of Impregnated Wood [g] | Before Exp. [g] | After Exp. [g] | Decrease Rate [%] |
|---|---|---|---|
| palustris | 65.72 | 68.86 | +4.48 |
|  | 61.73 | 67.22 | +8.90 |

In addition, the weights of the wood samples were measured after the wood samples were dried so as to check how much the wood samples were eaten by the termites. As shown in Table 2 below, the weights of the dried wood samples of the Petri dishes of the *Tyromyces palustris* were decreased more than the weights of the wood samples of the Petri dishes of the *Trametes versicolor* (refer to FIGS. 5 and 6). This is because *Tyromyces palustris* makes wood very damp and changes the tissue of the wood into sponge tissue so that termites can easily eat the wood.

TABLE 2

| Weight after drying | Before Exp. [g] | After Exp. [g] | Decrease Rate [%] |
|---|---|---|---|
| Trametes versicolor | 12.07 | 10.67 | 3.31 |
|  | 16.05 | 14.47 | 9.84 |
|  | 14.72 | 13.47 | 8.49 |
| Tyromyces palustris | 11.37 | 9.90 | 12.93 |
|  | 14.83 | 13.54 | 8.70 |
|  | 17.78 | 16.81 | 5.46 |

Figure 3:
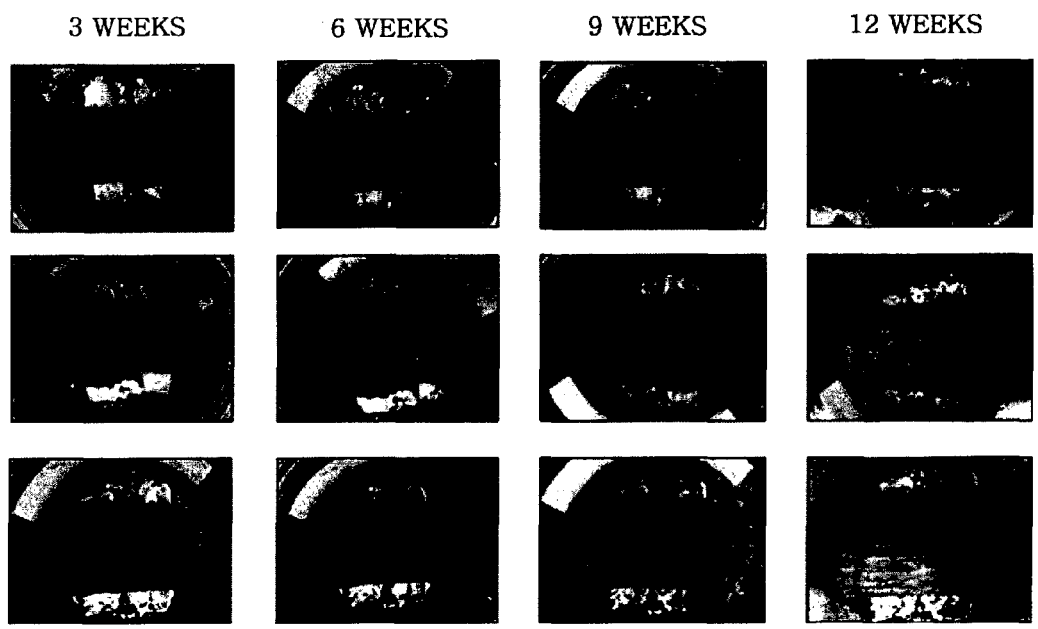
FIG. 3 shows images of *Trametes versicolor* and termites incubated together for twelve weeks to observe interactions between the *Trametes versicolor* and the termites.
Figure 4:
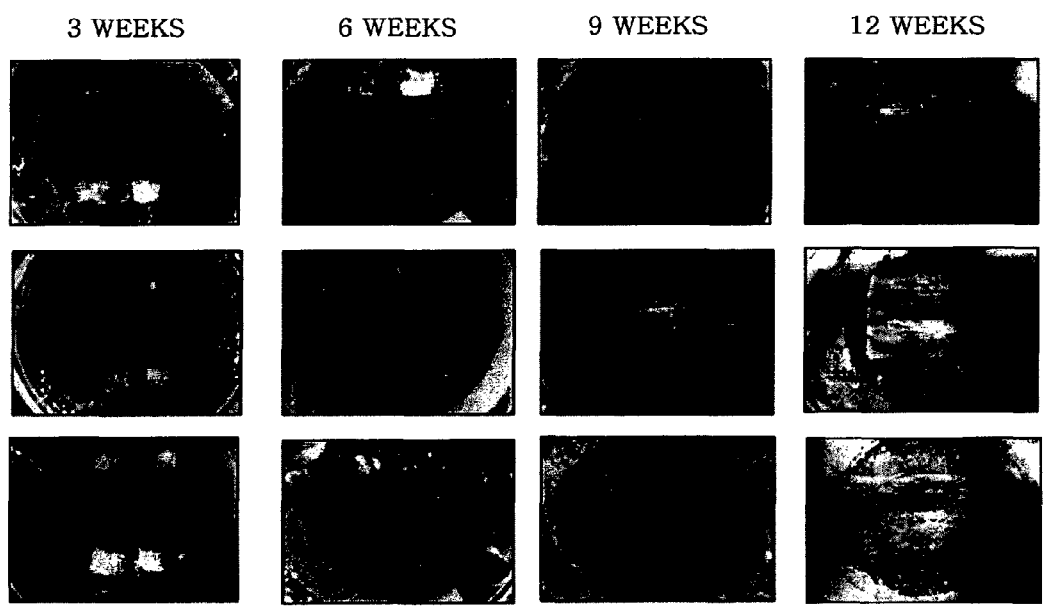
FIG. 4 shows images of *Tyromyces palustirs* and termites incubated together for twelve weeks to observe interactions between the *Tyromyces palustirs* and the termites.

In addition, as shown in FIGS. 3 and 4, the *Trametes versicolor* was not increased with time. However, the *Tyromyces palustris* was decreased with time, and finally the *Tyromyces palustris* was almost not shown. Therefore, it could be understood that wooden cultural assets and buildings might be damaged much more by the combination of termites and *Tyromyces palustris* (refer to FIGS. 3 and 4).

According to the present invention, termites can be reared indoors to observe physiological and ecological characteristics of the termites so as to use the observed data as reference material for controlling termites.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of rearing termites in a rearing box containing wood-rot fungus, comprising the steps of:
   (a) covering a bottom of the rearing box with soil to a thickness of 3 cm to 5 cm:
   (b) placing termites, a wood-rot fungus and a tree in a rearing box; and
   (c) maintaining the rearing box dark at a temperature of 20° C. to 25° C. and a humidity of 70% to 90%.

2. The method as set forth in claim 1, wherein the tree is prepared by sterilizing and drying a tree and impregnating the tree with distilled water in a vacuum.

3. The method as set forth in claim 1, wherein the temperature of the rearing box is maintained at 22° C. in the step (c).

4. The method as set forth in claim 1, wherein the humidity in the rearing box is maintained at a humidity of 80% in the step (c).

5. The method as set forth in claim 1, wherein the termites are included in the family rhinotermitidae.

6. The method as set forth in claim 1, wherein the termites are *Reticulitermes speratus* or *Reticulitermes speratus* kyushuensis Morimoto.

7. The method as set forth in claim 1, wherein the rearing box is 20 cm to 40 cm in length, 20 cm to 40 cm in width, and 30 cm to 50 cm in height.

8. The method as set forth in claim 1, wherein the rearing box is a box formed of a transparent acryl plate.

9. The method as set forth in claim 1, wherein the rearing box comprises a mesh cover.

10. The method as set forth in claim 1, wherein the wood-rot fungus is *Trametes versicolor* or *Tyromyces palustris*.

* * * * *